US006988317B2

(12) United States Patent
Sjölander et al.

(10) Patent No.: US 6,988,317 B2
(45) Date of Patent: Jan. 24, 2006

(54) VALVE INTEGRALLY ASSOCIATED WITH MICROFLUIDIC LIQUID TRANSPORT ASSEMBLY

(75) Inventors: Stefan Sjölander, Uppsala (SE); Thord Hansson, Bälinge (SE)

(73) Assignee: Biacore AB, Uppsala (SE)

( * ) Notice: Subject to any disclaimer, the term of this patent is extended or adjusted under 35 U.S.C. 154(b) by 170 days.

(21) Appl. No.: 10/715,880

(22) Filed: Nov. 18, 2003

(65) Prior Publication Data

US 2004/0148777 A1    Aug. 5, 2004

Related U.S. Application Data

(62) Division of application No. 10/001,246, filed on Nov. 1, 2001, now Pat. No. 6,698,454.

(60) Provisional application No. 60/245,865, filed on Nov. 2, 2000.

(51) Int. Cl.
    *B21K 1/20*     (2006.01)
(52) U.S. Cl. .............................. 29/890.127; 29/890.12; 29/890.131; 29/890.132; 29/890.14; 219/121.64
(58) Field of Classification Search ............. 29/890.12, 29/890.131, 890.132, 890.14, 890.127; 219/121.64; 137/885; 251/331, 61.1; 356/73, 318, 446; 250/458.1, 459.1
    See application file for complete search history.

(56) References Cited

U.S. PATENT DOCUMENTS 4,848,722 A  *  7/1989  Webster ...................... 251/61.1
4,852,851 A  *  8/1989  Webster ...................... 251/61.1
4,858,883 A  *  8/1989  Webster ...................... 251/61.1

(Continued)

OTHER PUBLICATIONS

Jönsson et al., "Real-time biospecific interaction analysis using surface plasmon resonance and a sensor chip technology," *Biotechniques* 11(5):620-7, Nov. 1991

*Primary Examiner*—Derris H. Banks
*Assistant Examiner*—Hung C. Le
(74) *Attorney, Agent, or Firm*—Seed IP Law Group PLLC

(57) ABSTRACT

The present invention discloses a valve integrally associated with a microfluidic transport assembly that is useful for regulating the flow of a liquid sample through an analytical instrument such as, for example, a biosensor. The valve integrally associated with a microfluidic liquid transport assembly, includes: a first rigid layer having substantially planar and opposing first and second surfaces; a second rigid layer having substantially planar and opposing third and fourth surfaces, the third surface of the second rigid layer being substantially coplanar and integrally bonded to the second surface of the first rigid layer; a first passageway defined by a groove, the groove being along the second surface of the first rigid layer and bounded by the third surface of the second rigid layer, the first passageway being adapted to flow a liquid sample therethrough, a valve seat having a substantially planar plateau surface, the valve seat being within the passageway and integrally connected to the first rigid layer such that the plateau surface is substantially planar to and interposed between the first and second surfaces of the first rigid layer; and a flexible membrane opposite the valve seat and integrally associated with a first membrane through hole of the second rigid layer, the flexible membrane having a passageway surface that is either (i) substantially coplanar to the second surface of the first rigid layer when the valve is in an open position, or (ii) bulged with a central portion thereof being substantially coplanar to the plateau surface of the valve seat when the valve is in a closed position. The present invention is also directed to methods of manufacturing of the same.

2 Claims, 4 Drawing Sheets

U.S. PATENT DOCUMENTS

| | | | |
|---|---|---|---|
| 5,313,264 A | * | 5/1994 | Ivarsson et al. .............. 356/73 |
| 5,443,890 A | * | 8/1995 | Ohman ....................... 428/167 |
| 5,496,009 A | * | 3/1996 | Farrell et al. .............. 251/61.1 |
| 5,542,444 A | * | 8/1996 | Alcock .......................... 137/1 |
| 5,593,130 A | * | 1/1997 | Hansson et al. ........... 251/61.1 |
| 5,653,259 A | * | 8/1997 | Ramstad ..................... 137/606 |
| 5,660,370 A | | 8/1997 | Webster ................. 251/129.17 |
| 5,743,295 A | * | 4/1998 | Alcock et al. .............. 137/519 |
| 5,962,081 A | * | 10/1999 | Ohman et al. .............. 427/534 |
| 5,967,163 A | * | 10/1999 | Pan et al. ...................... 137/1 |
| 6,089,538 A | * | 7/2000 | Shirkhan ............... 251/129.17 |

\* cited by examiner

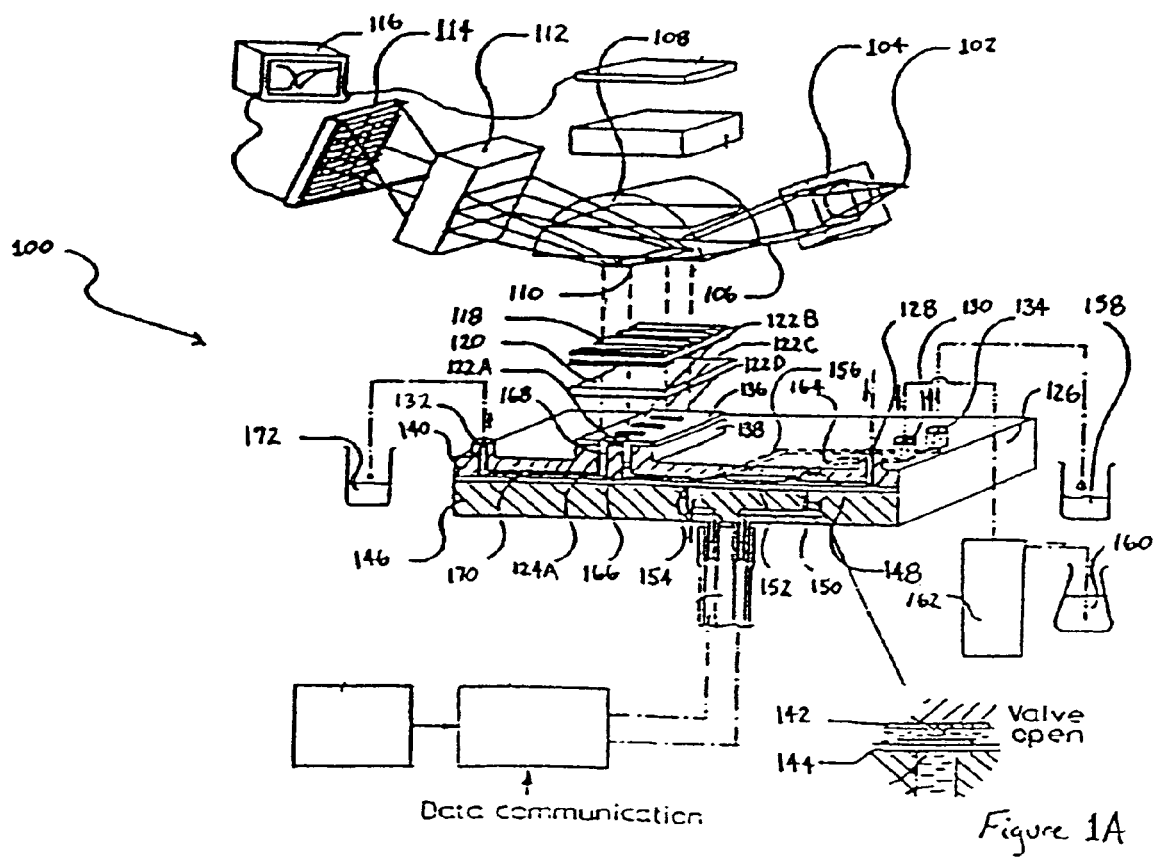
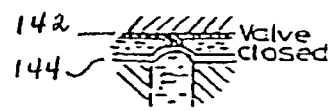
Figure 1 (Prior Art)
Figure 1A
Figure 1B

PLATE #1

RUBBER INLET

PLATE #2

FLOW CELL 532

PLATE #3

642 LIQUID CONNECTION
644 AIR CONNECTION
PLATE #4

VALVE INTEGRALLY ASSOCIATED WITH MICROFLUIDIC LIQUID TRANSPORT ASSEMBLY

CROSS-REFERENCE TO RELATED APPLICATIONS

This application is a divisional of U.S. patent application Ser. No. 10/001,246 filed Nov. 1, 2001, now U.S. Pat. No. 6,698,454, which claims the benefit under 37 USC 119(e) of U.S. Provisional Application No. 60/245,865, filed Nov. 2, 2000, which applications are incorporated herein by reference in their entirety.

BACKGROUND OF THE INVENTION

1. Field of the Invention

The present invention relates to valves associated with microfluidic assemblies, and more specifically, to valves integrally associated with microfluidic assemblies adapted to transport liquid samples for analytical purposes.

2. Description of the Prior Art

A variety of analytical instruments are used to characterize liquid samples containing an analyte of interest, particularly in the context of assays directed to real-time detection of biomolecular interactions. For example, the study of real-time biomolecular interactions through use of "biosensors" are now of fundamental importance in many fields, including biology, immunology and pharmacology. In this context, many biosensor-based analytical instruments include "microfluidic structures" adapted to transport one or more liquid samples through an interaction or a detection zone. Such microfluidic structures generally include a block unit that has multiple internal channels, inlet and outlet ports, pumps and valves; all of which operate in concert to flow small volumes of liquid sample and various other buffers and reagents through one or more interaction and/or detection zones.

An exemplary microfluidic structure for such liquid handling may be illustrated in the context of biosensors that use surface plasmon resonance (SPR) to monitor the interactions between an analyte and a ligand bound to a solid support. In this regard, a representative class of biosensor instrumentation is sold by Biacore AB (Uppsala, Sweden) under the trade name BIAcore® (hereinafter referred to as "the BIAcore instrument"). The BIAcore instrument includes a light emitting diode, a sensor chip covered with a thin gold film, an integrated microfluidic cartridge and photo detector. Incoming light from the diode is reflected in the gold film and detected by the photo detector. At a certain angle of incidence ("the SPR angle"), a surface plasmon wave is set up in the gold layer, which is detected as an intensity loss or "dip" in the reflected light. The theoretical basis behind the BIAcore instrument has been fully described in the literature (see, e.g., Jönsson, U. et al., *Biotechniques* 11:620–627, 1991).

More specifically, and as best shown in FIG. 1 (prior art), a representative BIAcore instrument 100 comprises a source of light 102, first lens means 104 for directing a transversely extending convergent beam 106 toward a prism 108 whereby the beam is focused in the bottom surface of the prism 108 to thus form a streak 110 of light. Rays of light reflected from the sensitized surfaces are imaged via an anamorphic lens system 112 on a two-dimensional photodetector device 114. The electronic signals created by the photodetectors are processed in an evaluation device 116 in the form of a computer.

By means of the prism 108 and an opto-interface 118 light from streak 110 is directed to a sensor unit 120 which lies in contact with a number of parallel, upwardly open portions 122A–D of flow channels 124A–D, respectively; only one of which, 124A, is shown. The flow channels form part of a block unit 126 for liquid handling, this block unit is shown with schematically indicated inlet connection tubes 128 and 130 and outlet connection tubes 132 and 134. A more complete description of this representative BIAcore instrument including its microfluidic block unit for flowing solutions therein may be found in U.S. Pat. No. 5,313,264, which is incorporated herein by reference in its entirety.

As more fully described in U.S. Pat. No. 5,313,264, and as also best seen in FIG. 1 (prior art), the upwardly open portions 122A–D of flow channels 124A–D (only flow channel 124A is shown) correspond to a first layer 136 of a sealing elastomer material (e.g., silicone rubber or the like) that has a number of cuts or slits extending therethrough. The first layer 136 has been cast onto a plateau 138 which is integral with a base plate 140. The base plate 140 is preferably a solid member made of, for example, plastic, metal, ceramics, or the like.

As best seen in corresponding FIGS. 1A and 1B, a second layer 142 of an elastomer material (e.g., silicone rubber or the like) has been applied by, for example, casting to the underside of base plate 140. The second layer 142 is provided with a system of flow channels or conduits formed by casting. A third layer 144, preferably of the same material as that of second layer 142, has been cast onto a support plate 146 made of a solid material (preferably made of the same material as that of base plate 140).

In view of the foregoing description, it will be readily understood that when the BIAcore instrument 100 is in an operable configuration such that the sensor unit 120 is pressed against first layer 136 by the opto-interface 118, the upwardly open portions 122A–D in first layer 136 will be sealed in liquid-tight relationship against sensor unit 120 and form four flow cells. For sake of simplicity, these four flow cells are also designated 122A–D.

Moreover, in operation, a liquid sample is made to flow through one or more of the flow cells 122A–D. More specifically, a pump (not shown) pumps the liquid sample to inlet tube 128, through an inlet channel 148, through an open valve 150, and then through a primary channel 152 having a fixed and well-defined volume, until it reaches a closed valve 154. The closed valve 154 directs the liquid sample into a waste channel 156 communicating via outlet connecting tube 134 with a disposal receptacle 158.

Next, a valve (not shown) at the upstream end of waste channel 156 is closed, and at the same time valve 150 is also closed. The liquid sample in the primary volume is now ready to be pumped into the flow cell 122A. This is done with the aid of an eluent solution 160 which is pumped by a pump 162 through inlet tube 130 to an eluent conduit 164 ending in a valve (not shown) which is now opened together with valve 154. Continued pumping of the eluent solution 160 causes the advancing eluent solution to press forward against the primary volume of the liquid sample and force it to advance upwardly through a riser duct 166 in the plateau 138, and then into flow cell 122A, and then down through a second riser duct 168 and out through an exhaust duct 170 and an outlet tube 132. From the outlet tube 132, the sample liquid followed by the eluent solution is directed to a waste disposal receptacle 172. When the sample liquid, which has a predetermined volume and/or flow rate, is flowing along flow cell 122A, the chemical interaction between the sample liquid and the sensing surface of the sensor unit 120 is optically detected and analyzed.

One aspect associated with the above-described microfluidic structure, however, lies with the second elastomeric layer 142 (FIGS. 1A and 1B), which elastomeric layer forms part of the valves. In general, the elastomeric layer has low chemical resistance, and may have high permeability with respect to certain gases and small molecules. Both of these attributes are less than optimal in certain embodiments. Accordingly, there is a need in the art for improved microfluidic structures adapted to transport liquid samples for analytical purposes. The present invention fulfills these needs, and provides for further related advantages.

BRIEF SUMMARY OF THE INVENTION

The present invention discloses a valve integrally associated with a microfluidic transport assembly that is useful for regulating the flow of a liquid sample through an analytical instrument such as, for example, a biosensor. The valve integrally associated with a microfluidic liquid transport assembly includes: a first rigid layer having substantially planar and opposing first and second surfaces; a second rigid layer having substantially planar and opposing third and fourth surfaces, the third surface of the second rigid layer being substantially coplanar and integrally bonded to the second surface of the first rigid layer; a first passageway defined by a groove, the groove being along the second surface of the first rigid layer and bounded by the third surface of the second rigid layer, the first passageway being adapted to flow a liquid sample therethrough, a valve seat having a substantially planar plateau surface, the valve seat being within the passageway and integrally connected to the first rigid layer such that the plateau surface is substantially planar to and interposed between the first and second surfaces of the first rigid layer; and a flexible membrane opposite the valve seat and integrally associated with a first membrane through hole of the second rigid layer, the flexible membrane having a passageway surface that is either (i) substantially coplanar to the second surface of the first rigid layer when the valve is in an open position, or (ii) bulged with a central portion thereof being substantially coplanar to the plateau surface of the valve seat when the valve is in a closed position. The present invention is also directed to methods of manufacturing of the same.

BRIEF DESCRIPTION OF THE DRAWINGS

FIG. 1 illustrates a schematic exploded view of a representative optical biosensor in accordance with the prior art.

FIG. 1A illustrates a partial cross-sectional view of FIG. 1 showing a valve in its open position.

FIG. 1B illustrates a corresponding cross-sectional alternative view showing the valve in its closed position.

DETAILED DESCRIPTION OF THE INVENTION

As mentioned above, the present invention relates to valves associated with microfluidic assemblies, and more specifically, to valves integrally associated with microfluidic assemblies adapted to transport liquid samples for analytical purposes. Although many specific details of certain embodiments of the invention are set forth in the following detailed description and accompanying Figures, those skilled in the art will recognize that the present invention may have additional embodiments, or that the invention may be practiced without several of the details described herein.

In the several embodiments set forth below, the inventive valves of this invention are integrally associated with microfluidic liquid transport assemblies, such as, for example, those adapted for use with "biosensors." As is appreciated by those skilled in the art, biosensors are analytical devices for analyzing minute quantities of sample solution having an analyte of interest, wherein the analyte is analyzed by a detection device that may employ a variety of detection methods. Typically, such methods include, but are not limited to, mass detection methods, such as piezoelectric, optical, thermo-optical and surface acoustic wave (SAW) device methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging, such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers. One exemplary biosensor is disclosed in U.S. Pat. No. 5,313,264 (assigned to Biacore AB, Uppsala, Sweden), which is incorporated herein by reference in its entirety.

Figures 2, 3:
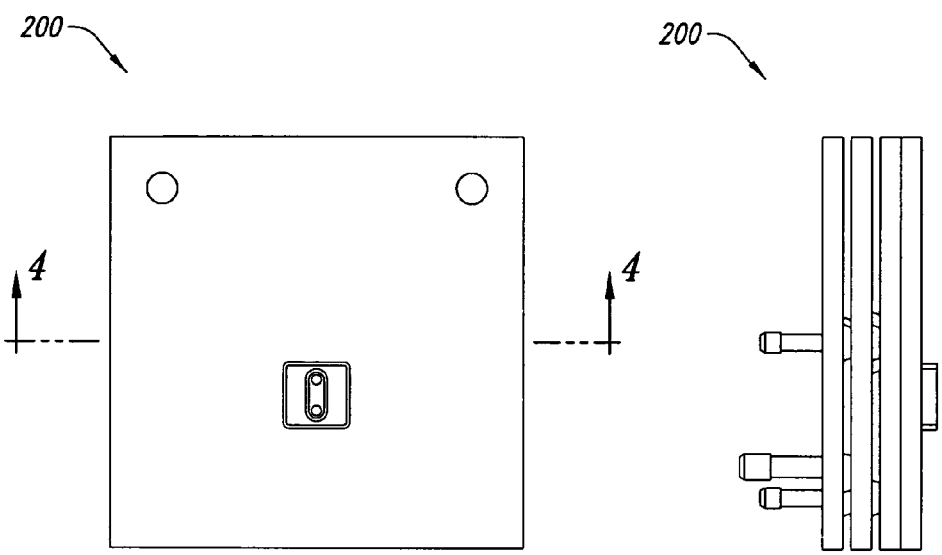
FIG. 2 illustrates a front elevational view of a microfluidic assembly in accordance with the present invention.
FIG. 3 illustrates a side elevational view of the microfluidic assembly shown in FIG. 2.
Figure 4:
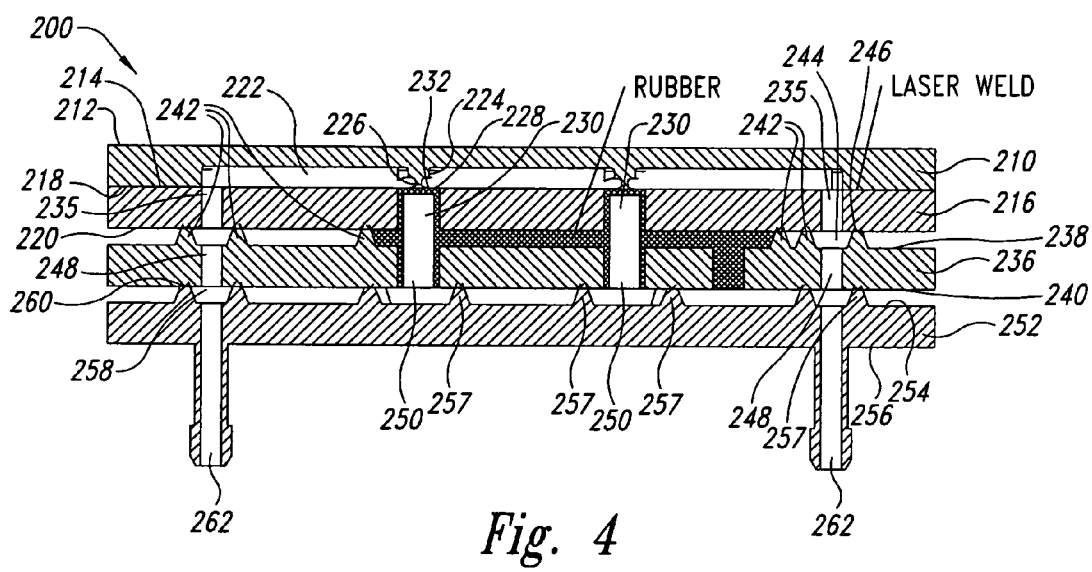
FIG. 4 illustrates a cross-sectional view of the microfluidic assembly shown in FIG. 2 taken along line 4—4.

In one embodiment of the present invention, and as best seen in FIGS. 2–4, a valve integrally associated with a microfluidic liquid transport assembly 200 includes a first rigid layer 210 having substantially planar and opposing first and second surfaces, 212 and 214, respectively, and a second rigid layer 216 having substantially planar and opposing third and fourth surfaces, 218 and 220, respectively. As shown in FIG. 4, the third surface 218 of the second rigid layer 216 is substantially coplanar and integrally bonded to the second surface 214 of the first rigid layer 210. As further shown in FIG. 4, the valve integrally associated with the microfluidic liquid transport assembly 200 further includes a first passageway 222 that is defined by a groove positioned along the second surface 214 of the first rigid layer 210 and bounded by the third surface 218 of the second rigid layer 216; the groove is defined by two opposing walls and a floor. A characteristic of this first passageway 222 is that it is adapted to flow a liquid sample therethrough.

Within the first passageway 222 and integrally connected to the first rigid layer 210, is a valve seat 224 that has a substantially planar plateau surface 226. The plateau surface 226 is substantially planar to and interposed between the first and second surfaces 212, 214. As shown in FIG. 4, the valve seat protrudes from the floor of the groove. A flexible membrane 228 is positioned opposite the valve seat 224; the flexible membrane 228 is integrally associated with one or more first flexible membrane through holes 230 of the second rigid layer 216. A characteristic of this flexible membrane 228 is that it has a passageway surface 232 that is either (i) substantially coplanar to the second surface of the first rigid layer when the valve is in an open position, or (ii) bulged with a central portion thereof being substantially coplanar to the plateau surface 226 of the valve seat 224 when the valve is in a closed position.

In further embodiments and as also shown in FIG. 4, the valve integrally associated with the microfluidic transport assembly 200 includes a plurality of first through holes 235 positioned such that they communicate with the first passageway 222. In still further embodiments, the valve integrally associated with the microfluidic transport assembly 200 includes a third rigid layer 236 that has substantially planar and opposing fifth and sixth surfaces, 238 and 240, respectively. The fifth surface 238 has a plurality of ridges 242 protruding therefrom, wherein the plurality of ridges 242 defines a second passageway 244 that is also adapted to flow a liquid sample therethrough. In addition, the plurality of ridges 242 also defines a top ridge surface 246 that is substantially coplanar and integrally bonded to the fourth surface 220 of the second rigid layer 216.

The third rigid layer 236, similar to the second rigid layer 216, includes a plurality of second through holes 248 positioned such that they communicate with the second passageway 244. As shown in FIG. 4, the third rigid layer 236 also includes one or more second flexible membrane through holes 250 that communicate with the flexible membrane 230 of the second rigid layer 216. The one or more third flexible membrane through holes 250 each have an additional amount of the flexible membrane 228 coextensively disposed about its respective wall.

In still further embodiments, the valve integrally associated with the microfluidic transport assembly 200 includes a fourth rigid layer 252 that has substantially planar and opposing seventh and eighth surfaces, 254 and 256, respectively. The seventh surface 254 has a plurality of second ridges 257 protruding therefrom, wherein the plurality of second ridges 257 defines a third passageway 258 that is also adapted to flow a liquid sample therethrough. In addition, the plurality of second ridges 257 also defines a top ridge surface 260 that is substantially coplanar and integrally bonded to the sixth surface 240 of the third rigid layer 236. The fourth rigid layer 252, similar to the second and third rigid layers 216, 236, includes a plurality of third through holes 262 positioned such that they communicate with the first, second, and third passageways, 222, 244, 258.

The component parts associated with the microfluidic transport assembly of the present invention may be processed and assembled together as set forth in the below-described exemplary manufacturing techniques, wherein the component parts and their associated features have dimensions as set forth below in Table 1.

TABLE 1

| REPRESENTATIVE DIMENSIONS OF THE COMPONENT PARTS | |
|---|---|
| Flow channels in plate #4: | 0.3 × 0.2 mm |
| Flow cell in plate #4: | 0.5 × 0.05 mm |
| Riser ducts: | 0.3 mm |
| Distance from valve seat to membrane surface: | 0.05 mm |
| Membrane valve outer diam.: | 0.6 mm |
| Membrane valve inner diam.: | 0.5 mm |
| Elastomer conduits between plate #1 and #2: | 0.7 × 0.4 mm |
| Pressure conduits between plate #2 and #3: | 0.7 × 0.4 mm |
| Plate thickness: | 1–2 mm |
| Ridges on plate #2 and #3 height: | 0.6 mm |

Figure 5:
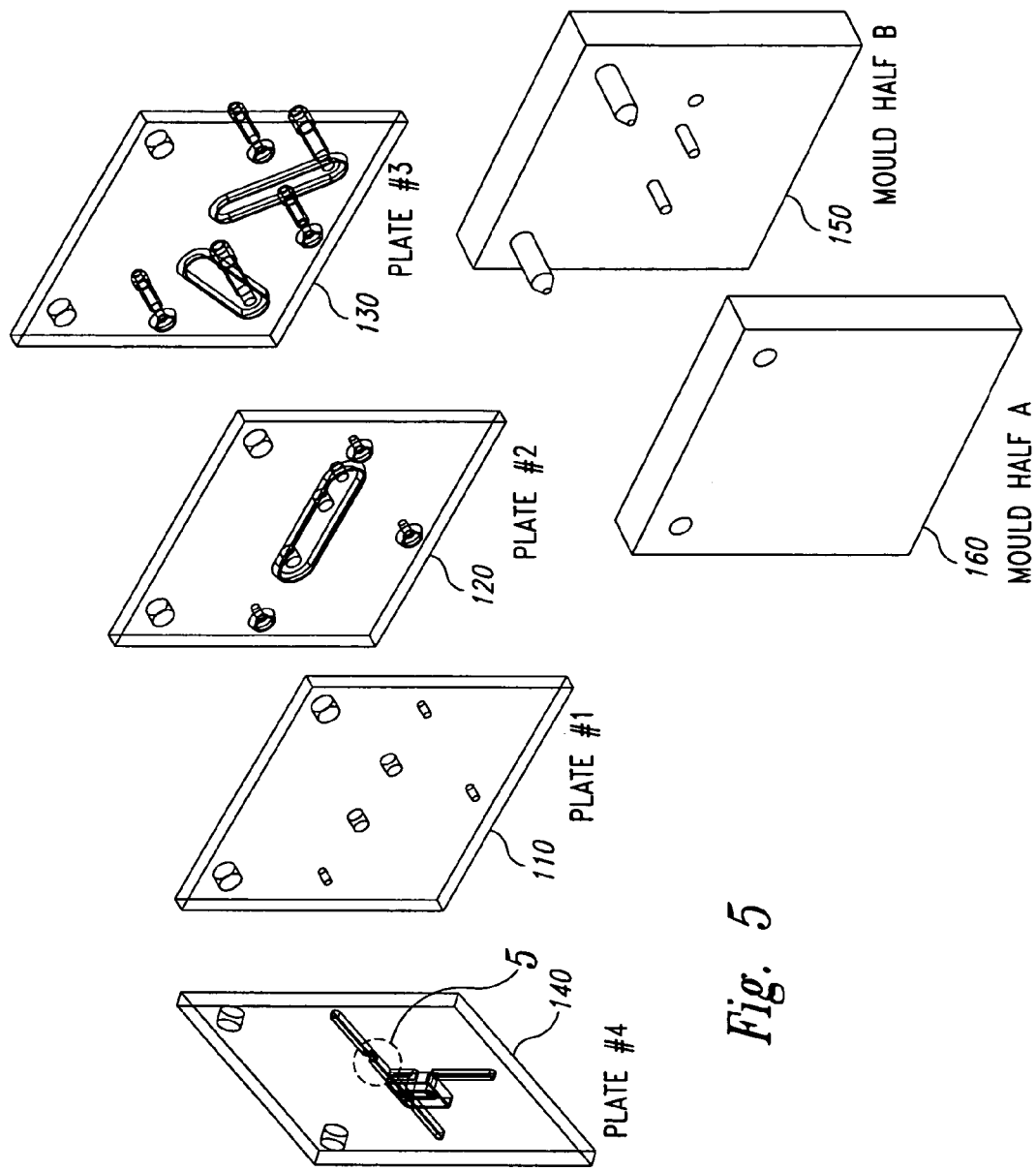
FIG. 5 illustrates an exploded isometric view of several plates that make up a microfluidic assembly in accordance with the present invention, and which are shown together with an exploded isometric view of a mold suitable for injecting an elastomeric material that forms a valve integrally associated with the microfluidic assembly.
Figure 6:
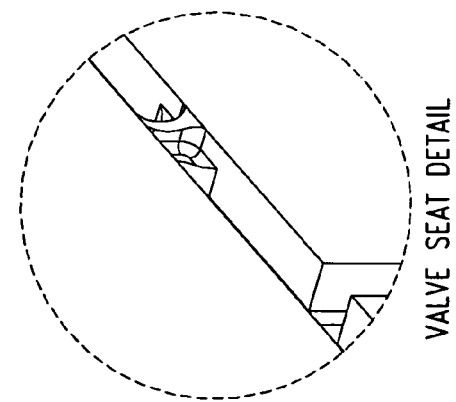
FIG. 6 is an enlarged view of the valve seat shown in FIG. 5.
Figure 7A:
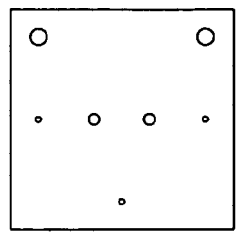
FIGS. 7A–C depict front, side, and back elevational views of a first plate associated with a microfluidic assembly in accordance with the present invention.
Figure 7B:
Figure 7C:
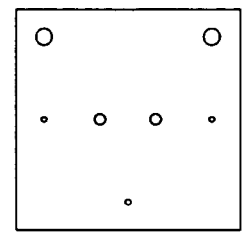

With regards to the exemplary manufacturing techniques, reference is also made to FIGS. 5 and 6, wherein FIG. 5 illustrates an exploded isometric view of several plates (i.e., plates 1–4) that make up a microfluidic assembly in accordance with the present invention, and which are shown together with an exploded isometric view of a two-part mold suitable for injecting/casting an elastomeric material that forms a valve integrally associated with the microfluidic assembly, and wherein FIG. 6 is an enlarged view of the valve seat shown in FIG. 5. Reference is also made to FIGS. 7A–C through FIGS. 10A–C, which Figures depict front, side, and back elevational views of the four plates (which plates constitute the above-described four rigid layers).

More specifically, a first flat plastic plate (shown as plate #1 in FIG. 5 and in FIGS. 7A–C, which plate #1 corresponds to the above-described second rigid layer) is plasma processed on one side so as to enhance bonding or adhesion of a later added flexible membrane such as, for example, a flexible membrane made of a silicone rubber or a thermoplastic elastomer (TPE). In general, the first flat plastic plate is preferably made with an IR-absorbing plastic material such as, for example, a polycarbonate tinted with carbon black. Thus, it is to be understood that the term "flexible" as used within the context of the present invention is to be construed broadly in that it denotes a membrane having pliable or elastomeric qualities. Similarly, the term "rigid" as used within the context of the present invention denotes a layer that is relatively stiff and unyielding.

Figure 8A:
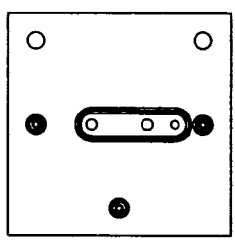
FIGS. 8A–C depict front, side, and back elevational views of a second plate associated with a microfluidic assembly in accordance with the present invention.
Figure 8B:
Figure 8C:
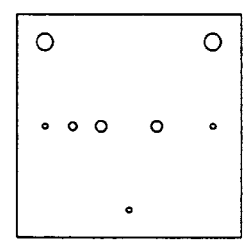

Concomitantly, a second flat plastic plate (shown as plate #2 in FIG. 5 and in FIGS. 8A–C, which plate #2 corresponds to the above-described third rigid layer) having generally the same hole pattern as that of the first flat plastic plate, and having a plurality of protruding ridges on one side that defines a planar top ridge surface, is connected together with the first flat plastic plate. That is, the plasma processed side of the first plate is connected together with the planar top ridge surface of the second plate such that each plate's respective hole patterns are in substantial axial alignment with each other. In general, the second flat plastic plate is preferably made with a non-IR-absorbing plastic material such as, for example, a polycarbonate.

The first and second plastic plates may be connected together by any of a number of suitable bonding techniques such as, for example, gluing or by an ultrasonic or laser welding technique. As is appreciated by those skilled in the art, laser welding offers significant advantages over conventional joining technologies; it is especially well suited for joining plastic materials having different optical absorptions at the laser wavelength. The laser light may penetrate the transparent component (e.g., plate #1) and is then absorbed by the non-transparent component (e.g., plate #2) where it is converted into heat. The first and second plastic plates melt at the interface and welding may be effected by external pressure applied by a workholding fixture. In this manner, a welded unit (also referred to as a membrane plate) inclusive of the first and second flat plastic plates (i.e., second and third rigid layers, respectively) may be formed.

The formed welded unit may then be placed in a mold that consists of two halves (shown in FIG. 5 as mould half A and mould half B) to facilitate formation of an internal flexible membrane that defines part of the valve. More specifically, the welded unit may be placed in the two-part mold, wherein mould half A has a smooth mold surface and mould half B has a smooth mold surface with one or more perpendicularly protruding cylinders that are adapted to concentrically fit within the flexible membrane through holes associated with plate #1 and plate #2. In general, the protruding cylinders have flat top surfaces, are preferably about 0.1 mm shorter than the thickness of the welded unit, and have diameters that are preferably about 0.1 less than the diameters of the flexible membrane through holes. A silicone rubber (preferably having Shore A hardness of between 24–29) or a thermoplastic elastomer (TPE) in liquid form may then be injected through a funnel associated with mould half B so as to form via casting the internal flexible membrane. As is appreciated by those skilled in the art, casting is the process whereby a liquid is poured into a mold and allowed to react, cure, or harden to form a solid object in the shape of the mold cavity. Moreover, it is to be understood that suitable thermoplastic elastomers for purposes of the present invention include a thermoplastic polyurethane elastomer (i.e., TPU), a polyolefin-based thermoplastic elastomer (i.e., TPO), a thermoplastic elastomer based on dynamically vulcanized elastomer-thermoplastic blends (i.e., TPV), a styrene block thermoplastic elastomer, a thermoplastic polyether ester elastomer, a thermoplastic elastomer based on halogen-containing polyolefins, and a thermoplastic elastomer based on polyamides, as well as various combinations and blends thereof.

Figure 9A:
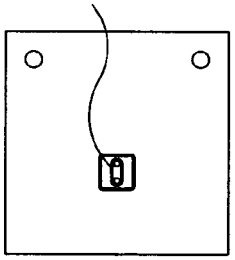
FIGS. 9A–C depict front, side, and back elevational views of a third plate associated with a microfluidic assembly in accordance with the present invention.
Figure 9B:
Figure 9C:
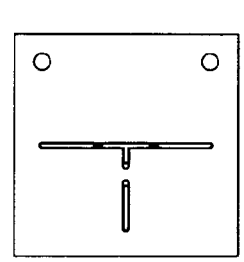
Figure 10A:
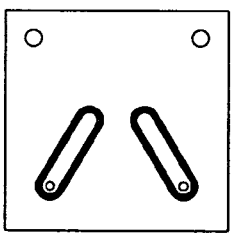
FIGS. 10A–C depicts an elevational views of a fourth plate associated with a microfluidic assembly in accordance with the present invention.
Figure 10B:
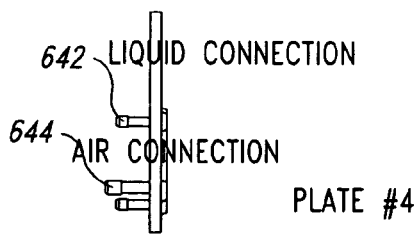
Figure 10C:
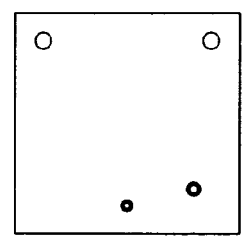

After solidification of the silicone rubber or suitable thermoplastic elastomer (TPE), the welded unit may then be removed from the mold, and any burrs that exist may be eliminated. A third flat plastic plate having a channel pattern of ridges leading to each membrane valve (shown as plate #3 in FIG. 5 and in FIGS. 9A–C, which plate corresponds to the above-described fourth rigid layer) may then be connected together with the welded unit to form a three-plate assemblage referred to as the valve plate. Next, a fourth plastic plate having a channel pattern of grooves with valves seats (shown as plate #4 in FIG. 5 and in FIGS. 10A–C, which plate corresponds to the above-described first rigid layer) may then be connected together with the valve plate to form the valve integrally associated with the microfluidic transport structure in accordance with the present invention by a suitable bonding technique, such as, for example, gluing or by an ultrasonic or laser welding technique.

By this exemplary method, a valve integrally associated with a microfluidic transport structure assembly may be manufactured that overcomes many of the drawbacks associated with prior art microfluidic structures. In particular, the surface area of the elastomeric layer that comes into contact with the liquid sample may now be minimized, thereby reducing adverse chemical interactions that may occur between the liquid sample and the elastomeric layer. Other advantages include a more streamlined manufacturing process.

While the valves integrally associated with microfluidic transport assemblies of the present invention and their representative manufacturing techniques have been described in the context of the embodiments illustrated and described herein, the invention may be embodied in other specific ways or in other specific forms without departing from its spirit or essential characteristics. Therefore, the described embodiments are to be considered in all respects as illustrative and not restrictive. The scope of the invention is, therefore, indicated by the appended claims rather than by the foregoing description, and all changes that come within the meaning and range of equivalency of the claims are to be embraced within their scope.

What is claimed is:

1. A method for manufacturing a valve integrally associated with a microfluidic transport assembly, the method comprising the steps of:

integrally bonding a first rigid layer having substantially planar and opposing first and second surfaces to a second rigid layer having substantially planar and opposing third and fourth surfaces, such that the third surface of the second rigid layer contacts the second surface of the first rigid layer, and such that a first passageway is formed wherein the first passageway is defined by a groove that runs along the second surface of the first rigid layer and is bounded by the third surface of the second rigid layer, and wherein the first passageway is adapted to flow a liquid sample therethrough, and wherein the first passageway includes a valve seat that has a substantially planar plateau surface wherein the valve seat is integrally connected to the first rigid layer such that the plateau surface is substantially planar to and interposed between the first and second surfaces of the first rigid layer; and casting a flexible membrane into a first membrane through hole of the second rigid layer such that the flexible membrane has a passageway surface that is adapted to be either (i) substantially coplanar to the second surface of the first rigid layer when the valve is in an open position, or (ii) bulged with a central portion thereof being substantially coplanar to the plateau surface of the valve seat when the valve is in a closed position.

2. The method of claim 1 wherein the step of integrally bonding involves laser welding the third surface of the second rigid layer to the second surface of the first rigid layer.

* * * * *